(12) United States Patent
Barie et al.

(10) Patent No.: US 6,974,707 B1
(45) Date of Patent: Dec. 13, 2005

(54) DEXTRAN-COATED SURFACE

(75) Inventors: Nicole Barie, Stutensee (DE); Jean Gobet, Cordelles (CH); Michael Rapp, Eppelheim (DE); Hans Sigrist, Kernenried (CH)

(73) Assignees: Forschungszentrum Karlsruhe GmbH, (DE); Centre Suisse d'Electronique et de Microtechnique S.A., (CH)

( * ) Notice: Subject to any disclaimer, the term of this patent is extended or adjusted under 35 U.S.C. 154(b) by 0 days.

(21) Appl. No.: 09/694,241

(22) Filed: Oct. 23, 2000

Related U.S. Application Data

(63) Continuation-in-part of application No. PCT/EP99/02599, filed on Apr. 19, 1999.

(30) Foreign Application Priority Data

Apr. 24, 1998 (DE) .............................. 198 18 360

(51) Int. Cl.⁷ .................... G01N 33/548; G01N 33/545
(52) U.S. Cl. ...................... 436/529; 436/531; 530/810; 530/811
(58) Field of Search ............... 422/68.1; 530/810–812; 436/164, 518, 524, 528, 529, 823; 435/4, 435/7.9, 7.92, 103, 174–180, 287.1, 287.2, 435/287.9, 288.7, 808, 7.1

(56) References Cited

U.S. PATENT DOCUMENTS

| | | | | |
|---|---|---|---|---|
| 5,154,808 A | * | 10/1992 | Miyasaka et al. | 204/157.15 |
| 5,436,161 A | | 7/1995 | Bergström et al. | 435/291 |
| 5,529,914 A | * | 6/1996 | Hubbell et al. | 264/4 |
| 5,563,056 A | * | 10/1996 | Swan et al. | 424/486 |
| 5,639,620 A | * | 6/1997 | Siiman et al. | 427/2.13 |
| 5,858,802 A | * | 1/1999 | Chai-Gao et al. | 422/57 |
| 5,986,066 A | * | 11/1999 | Barner et al. | 436/501 |
| 6,099,122 A | * | 8/2000 | Chabrecek et al. | 351/160 H |

FOREIGN PATENT DOCUMENTS

| | | | |
|---|---|---|---|
| EP | 0 124 676 A1 | * | 11/1985 |
| EP | 0 886 141 | | 12/1998 |
| WO | WO 90/04609 | | 5/1990 |
| WO | WO 91/16425 A1 | * | 10/1991 |
| WO | WO 92/21976 | | 12/1992 |
| WO | WO 96/31557 A1 | * | 10/1996 |
| WO | WO 97/43631 | * | 11/1997 |

OTHER PUBLICATIONS

Sigrist et al. Surface immobilization of biomolecules by light. Optical Engineering. (Aug. 1995) vol. 34, No. 8, pp. 2339-2348.*

Sigrist et al. Light-dependent, covalent immobilization of biomolecules on 'inert' surfaces. Bio/Technology (Sep. 1992) vol. 10, pp. 1026-1028.*

Barie, N. et al. "Covalent Photolinker-Mediated Immobilization of an Intermediate Dextran Layer to Polymer-Coated Surfaces for Biosensing Applications", *Biosens. Bioelectron.* (1998) 13(7-8) 855-860.

* cited by examiner

*Primary Examiner*—James Housel
*Assistant Examiner*—Shafiqul Haq
(74) *Attorney, Agent, or Firm*—Steptoe & Johnson LLP

(57) ABSTRACT

In a dextran coated surface disposed on a carrier, the connections between the dextran and the carrier surface are formed by a photolinker, the dextran coating being attached to the carrier surface by co-immobilization of a mixture of dextran and the photolinker.

6 Claims, 4 Drawing Sheets

DEXTRAN-COATED SURFACE

This is a continuation-in-part application of international application PCT/EP99/02599 filed Apr. 19, 1999 and claiming the priority of German application 198 18 367.7 filed Apr. 24, 1998.

BACKGROUND OF THE INVENTION

The invention relates to a dextran coated surface as it is known from O'Shannessy, D. J., Brigham-Burke, M.; Peck, K.; Anal. Biochem. 205 (1992) 132–136.

It is known from S. Löfas, B. Johnson; J. Chem. Soc. Chem. Commun. (1990) 1526–1528 that dextrans can be attached to gold surfaces by way of self-assembled monolayers of 1,ω-hydroxy-alkylthiols.

However, some sensors such as surface acoustic wave sensors (SAW) do not permit the use of a conductive intermediate layer so that gold cannot be used as an intermediate layer.

Such sensors are known for example from DE 43 19 215 A1.

It is the object of the present invention to provide a layer by way of which a dextran layer can be fixed to a carrier surface.

SUMMARY OF THE INVENTION

In a dextran coated surface disposed on a carrier, the connections between the dextran and the carrier surface are formed by a photolinker, the dextran coating being attached to the carrier surface by co-immobilization of a mixture of dextran and the photolinker.

The layering according to the invention has the following advantages:

The extremely flexible dextran-containing layer can be used on SAW sensors and on many other sensors.

Almost all proteins can be immobilized on the dextran by a standardized method (i.e. carbodiimide-chemistry).

In place of dextran, any modified dextran species may be used such as carboxy-dextran, biotynilized dextran. Any other type of functionalized dextran, wherein one or several reactive groups are bonded to the dextran may also be used.

User of conventional biosensor systems do not need to adjust with respect to the sensor chemistry when introducing dextran-coated SAW biosensors.

Furthermore, this method is transferable to any other systems in a simple manner. Only a single protein (the BSA) needs to be modified, not the substance itself which is to be immobilized.

The T-BSA used for the photo-immobilization serves at the same time as means for blocking unspecified bonding locations on the surface provided with a protective coating.

With the aid of SAW sensor arrays, it is possible to detect at the same time different bio-components, whereby a whole class of substances can be screened. This is difficult to achieve with the commercially available biosensor systems (for example BIAcore or IAsys) because of the expensive optical methods.

Photoimmobilization is, in comparison to an attachment of the dextrans by way of thiols, a very simple and easily reproducible method.

Below an embodiment of the invention will be described on the basis of the accompanying drawings.

DESCRIPTION OF EMBODIMENTS OF THE INVENTION

Figure 1:
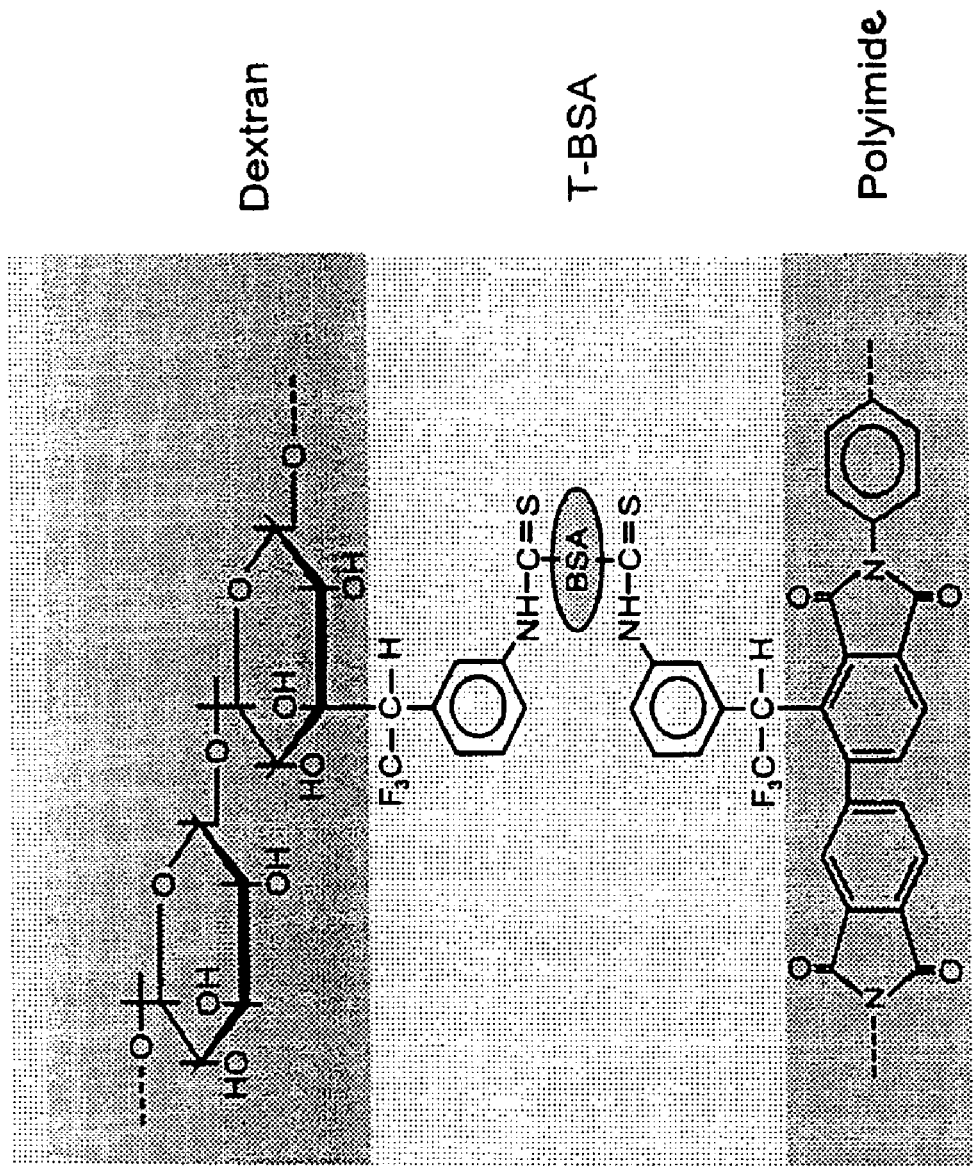
FIG. 1 shows schematically the layer arrangement and
FIG. 2, FIG. 3, and FIG. 4 show measurement results obtained with coated SAW sensors.

Protective Coatings:

In order to employ commercially available SAW-devices as mass-sensitive transducers in biosensors, the SAW surface must be coated with a bio-sensitive layer of proteins which then detect the respect analyte molecules in a sample.

These reactions take place in aqueous media. However, the use in these aqueous media and also the necessary immobilization procedures require a protection for the structures and bond wires of aluminum present on the device since, otherwise, they will not be able to withstand the chemical conditions.

DE 196 18 82 discloses a thin coating of a complete part with polyimide by a spin coating procedure which provides for a relatively good protection.

However, after operation of the part in acid or alkaline media substantial corrosion of the structures may occur.

An improved protection can be obtained by a coating with a thin film of parylene.

Parylene is a group designation for thermoplastic polymers with phenyl rests joined in the 1,4-position by way of ethylene-bridges. Parylenes are solvent resistant below their melting points; they have excellent dielectric properties and are excellent barrier plastics. They are mainly used as intermediate layers for isolators, for the passivation of semi-conductors and as smooth coatings of printed conductor plates.

They are manufactured by dehydrating dimerisation of p-xylol to paracyclophane by way of 1,4-chinodimethane, which is formed as an intermediate compound and which polymerizes during condensation from the gas phase on suitable substrates to form thin films of poly(p-xylene).

In addition to poly(p-xylylene) the parylenes poly(2-chlorine-p-xylylene)s and the poly(dichlorine-p-xylylene)s, which are accessible from the corresponding p-xylol-derivatives, are suitable for coatings.

The parylene-coated parts have a number of advantages over polyimide-coated parts.

The additional attenuation by the polymer layer deposited is small, but the amount is about the same for parylene and polyimide. The parts provided with a protective coating have attenuations of −2.5 to 3.0 dB (at a phase passage of −10°).

The reproducibility of the parylene coating is clearly better than the coating of the SAW devices with polyimide.

In contrast to a polyimide film, a parylene film is extremely smooth which is very important for the use of SAW components since the travel of the surface wave is disturbed by surface irregularities; they result in additional attenuation losses and in reduced sensitivity.

The protective coating is to protect the SAW component from the corrosive attack by aqueous solutions, acids, bases and other aggressive compounds.

With polyimide-coated components, the development of gases could be observed already after a few minutes particularly at the contact locations of the bond wires with the bond pads which appeared to be the result of a corrosive attack of the acids on the aluminum. After about 15–30 min, the bond wires were completely destroyed and the interdigital structure was clearly under attack.

In contrast, no attack could be observed with parylene-coated components even after exposure of several hours and even after heating of the sensor in acid. The parylene film therefore provides for excellent protection of the component from corrosion attacks.

Photoimmobilization of the Dextran:

FIG. 1 shows schematically the layer arrangement for the immobilization of biomolecules on dextran-coated SAW sensor surfaces by co-immobilization with photo-active T-BSA. As shown, the dextran is bonded covalently to the sensor surface, which is provided with a protection layer, by photo-co-immobilization with the aid of T-BSA.

For this covalent attachment, the following steps are performed:

A mixture of T-BSA and dextran is deposited on the sensor provided with a protective surface.

An incubation period of 60 min. at room temperature follows.

Then the preparation is dried in a vacuum for 2 hrs ($10^{-3}$ mbar) followed by a light exposure using a Hg vapor lamp.

T-BSA is produced from bovine serum albumin (BSA) by converting it with a diazirine-derivate, the 3-trifluoro-methyl-3-(m-isothiocyano-phenyl)-diazirine (TRIMID), whereby, as a result, an amino group of the lysine side chains of the photoactive TRIMID is introduced (M. Dolder, H. Michel, H. Sigrist, J. Prot. Chem. 9 (1990) 407–415 and Sigrist, H., Muhlmann, M.; Dolder, M.; J. Photochem. and photobiol., B 7 (1990), 277–287). Per molecule BSA up to 7 TRIMID-groups can be introduced in this way. If the T-BSA is then irradiated with light of the wave length 348 nm, the diazirine ring releases nitrogen and a triplett-carbene is formed. This triplett-carbene is very reactive and inserts itself in a multitude of chemical bonds.

In the co-immobilization the T-BSA serves as a photo crosslinker, that is, the BSA is deposited, together with dextran, on the SAW-component provided with a protective layer. Since—as mentioned earlier—per BSA molecule up to 7 TRIMID units are present, the triplett carbenes formed during the irradiation can provide for cross-links with the protective layer as well as with the dextrans. In this way, the dextran becomes covalently attached to the surface.

The co-immobilization of dextran by way of T-BSA has several advantages:

It involves a very simple and fast procedure. The T-BSA is mixed with the dissolved dextran and applied to the protective layer-coated component. Then the water is removed in a vacuum for 2 hours in order to ensure that the carbenes formed later during illumination react with polymer and dextran and not with any surrounding water. After the water is completely removed, the component is exposed to a Hg vapor lamp for 45 minutes. Consequently, after a total of only 4 hrs, the dextran is covalently attached to the surface.

Immobilization of Proteins on Dextran and Observation of the Immunoreaction:

In order to obtain a biosensor, the receptive biomolecule must be immobilized on the dextran. A simple and rapid attachment of almost any biomolecule is possible using the following procedure (Johnson, B.; Löfas, S.; Lindquist, G., Anal. Biochem. 198 (1991) 268–277).

1. The carboxy-methylized dextran attached by photoimmobilization to the protective layer-coated surface is converted to NHS-ester in a single-step activation by N-(3-Dimethylamino-propyl)-N'-ethyl carbodiimide (EDC) and N-hydroxysuccinimide (NHS). The NHS-esters are very reactive and have a half-life on the sensor surface of about 15 minutes. If then a biomolecule is added, it attaches with one of its amino groups to the dextran while releasing N-hydroxysuccinimide. During the single-step activation about 30 to 40% of the carboxy groups of the dextran are converted to NHS-ester; therefore, after the attachment of the biomolecules, the dextran still has a multitude of active NHS-ester groups. However, since for example, in the case of an immobilized antibody during the immunoreaction, the antigen is to be bound by the antibody and not covalently attached by way of the NHS-ester, the excess NHS esters must be deactivated. This is achieved with 1M ethanolamine. In the process, the NHS-esters are converted to 2-hydroxyethaneamid hydroxyethaneamid derivatives, whereby finally the finished biosensor is obtained.

Figure 2:
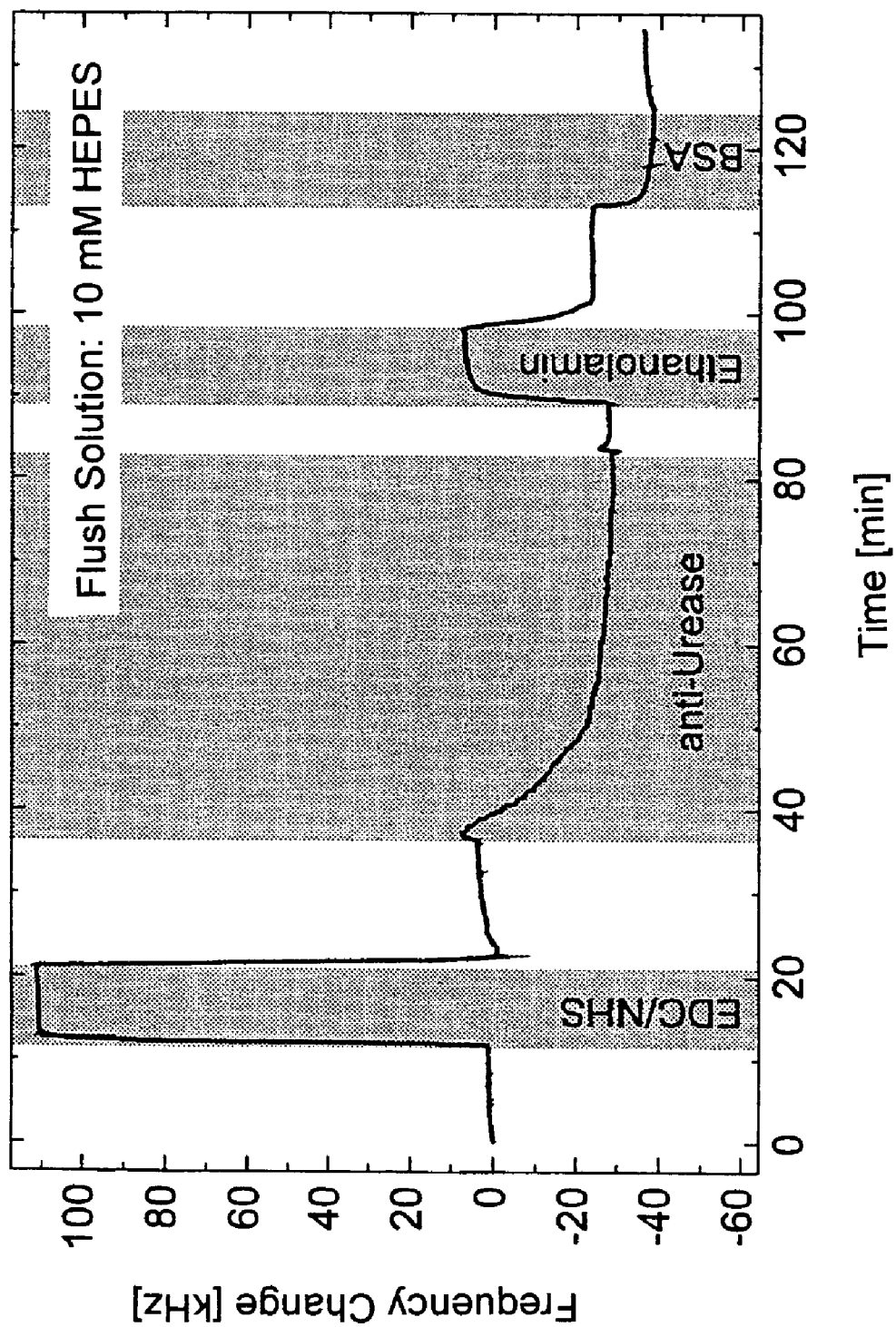

2. FIG. 2 shows, in an exemplary way, an immobilization with sensor response.

The sensor is first flushed with 10 mH HEPES-buffer (pH 7.5) in order to assume the basis line. The one-step activation occurs with a freshly prepared mixture of 100 mM NHS and 400 mM EDC. This solution has a conductivity of 14.4 mS/cm, which is substantially higher than the conductivity of 550 $\mu$S/cm of the HEPES buffer. The sensor reacts with a frequency increase of about 100 kHz. Subsequently, the sensor is again flushed with HEPES buffer and then a solution of the biomolecule to be immobilized is applied. The biomolecule—in the present case monoclonal antibodies against urease—is present in a 10 mM acetate buffer at a pH=5.0. FIG. 2 shows a frequency reduction, which is caused by the mass increase on the sensor surface. From the sensor behavior, the slow adjustment of the equilibrium is apparent which is reached after about 45 to 50 minutes. Then flushing with HEPES buffer takes place again. Subsequently, the excess NHS ester groups are de-activated by ethanolamine. In the last step for the preparation of the biosensor samples 4 mg/ml BSA are applied in order to block the non-specific binding sites.

Figure 3:
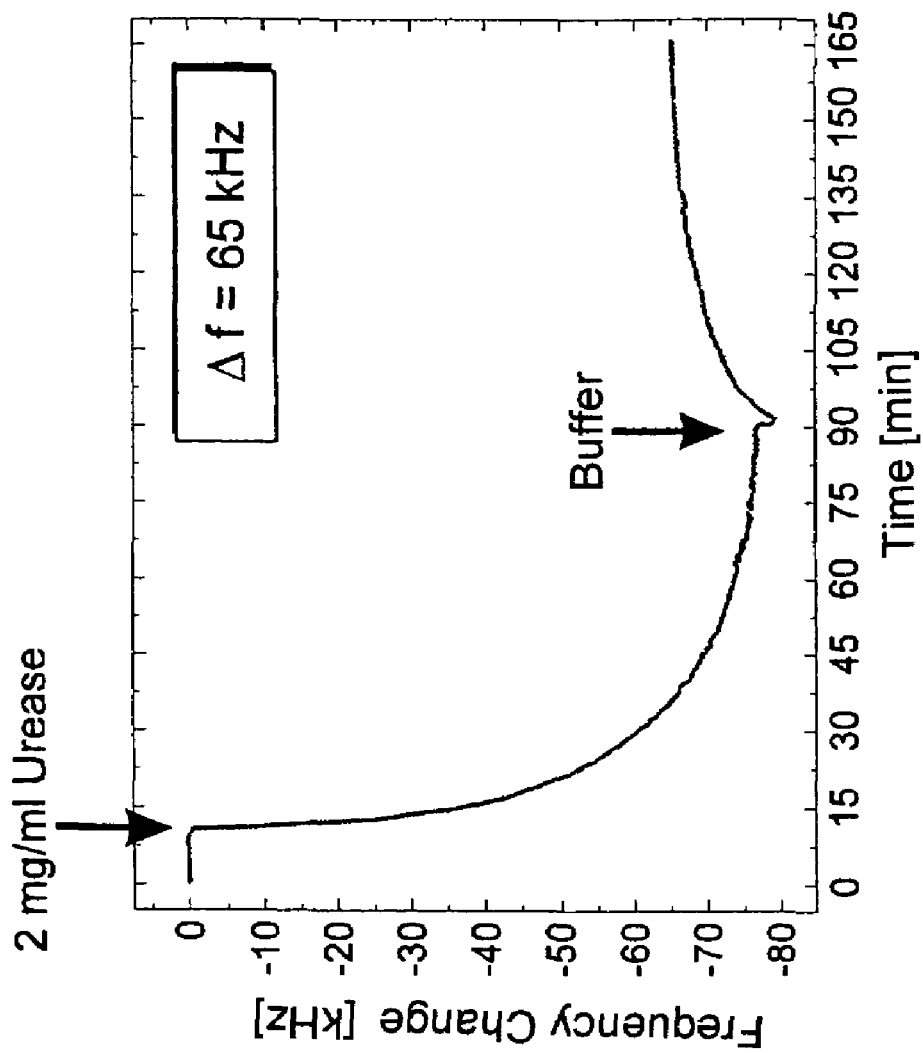

3. FIG. 3 shows the observation of an immunoreaction. With a sensor prepared as described above first tests for observing the immunoreaction were performed. For that purpose, a sensor coated with monoclonal antibodies against urease was first flushed with 10 mM HEPES buffer (pH 7.5) and the basis line was recorded. Subsequently, a solution of 2 mg/ml urease was applied. A frequency reduction is observed which ends after about 90 minutes. After further flushing with HEPES buffer a frequency change of about 65 kHz was obtained which is the result of the immunoreaction between the immobilized antibodies and the antigen urease.

Figure 4:
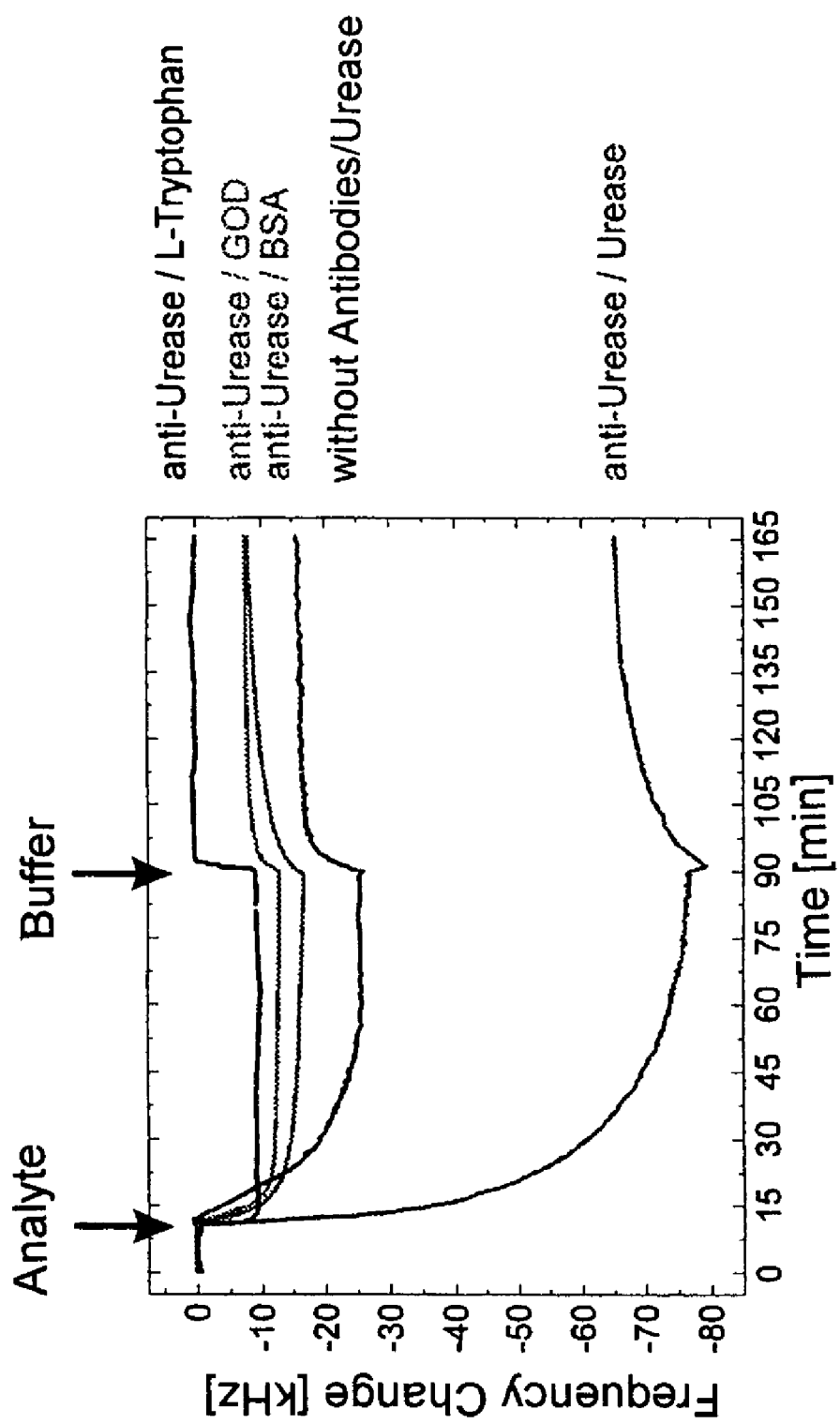

FIG. 4 shows control tests with non-specific antigens. A plurality of control experiments were performed. In this process, non-specific antigens were applied to sensors with identical treatment and the sensor response was observed. When such a sensor was exposed to immobilized monoclonal antibodies against urease with L-tryptophan, no frequency change was observed. The rapid but reversible frequency change when exposed to an analyte or during reverse flushing with buffer is caused by the different conductivity of the two solutions. Upon exposure to glucose oxidase (GOD) or respectively, BSA, a frequency change of about 8 kHz is obtained. A sensor, which has no immobilized antibodies on the dextran matrix showed, upon exposure to urease, a frequency change of about 15 kHz, which is the result of a non-specific reaction of urease. All these frequency changes are clearly lower than those of the specific immunoreaction between urease and antibodies against urease, which were determined to be 65 kHz.

What is claimed is:

1. A dextran-coated carrier having a surface with a connection between dextran disposed as coating on the carrier formed by a photolinker, said dextran coating being formed on and covalently attached to said carrier by co-immobilization resulting from a mixture of the dextran and a 3-trifluoromethyl-3-(m-isothiocyanophenyl)-diazirine (TRIMID)-modified aminodextran, wherein the dextran is attached to the carrier through a component resulting from the irradiation of the 3-trifluoromethyl-3-(m-isothiocyanophenyl)-diazirine (TRIMID)-modified aminodextran.

2. A dextran-coated surface according to claim 1, wherein said carrier surface is coated with a polymer film.

3. A dextran-coated surface according to claim 2, wherein said polymer film consists of one of polyimide and poly(p-xylylene).

4. A dextran-coated surface according to claim 1, wherein said carrier surface is a surface of a mass-sensitive sensor.

5. A dextran-coated surface according to claim 4, wherein said mass-sensitive sensor is surface acoustic waves conductive component.

6. A dextran-coated surface according to claim 1, wherein said carrier surface is a surface of an optical or electromechanical sensor.

* * * * *